(12) United States Patent
Senn et al.

(10) Patent No.: US 6,482,004 B1
(45) Date of Patent: Nov. 19, 2002

(54) LIGHT CURING DEVICE AND METHOD FOR CURING LIGHT-POLYMERIZABLE DENTAL MATERIAL

(75) Inventors: Bruno Senn, Buchs (CH); Gottfried Rohner, Altstatten (CH); Peter Burtscher, Nuziders (AT)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 09/534,954

(22) Filed: Mar. 24, 2000

Related U.S. Application Data
(60) Provisional application No. 60/146,590, filed on Jul. 30, 1999.

(30) Foreign Application Priority Data

Mar. 26, 1999 (DE) .......................................... 199 13 890

(51) Int. Cl.⁷ ............................................. A61C 13/15
(52) U.S. Cl. ........................ 433/29; 522/908; 315/291; 362/804
(58) Field of Search .......................... 433/29, 226, 229; 522/908; 315/291; 362/804

(56) References Cited

U.S. PATENT DOCUMENTS

| | | | | |
|---|---|---|---|---|
| 4,221,994 A | * | 9/1980 | Friedman et al. ............. 315/224 |
| 4,229,658 A | * | 10/1980 | Gonser ................... 250/504 H |
| 4,309,617 A | * | 1/1982 | Long ...................... 250/504 H |
| 4,450,139 A |   | 5/1984 | Bussiere et al. |
| 4,839,566 A | * | 6/1989 | Herold et al. ................. 31/308 |
| 5,049,068 A | * | 9/1991 | Sterrett et al. ................. 433/9 |
| 5,634,711 A | * | 6/1997 | Kennedy et al. ............. 362/119 |
| 5,912,470 A | * | 6/1999 | Eibofner et al. ......... 250/504 H |
| 5,975,895 A | * | 11/1999 | Sullivan ...................... 433/29 |
| 6,008,264 A | * | 12/1999 | Ostler et al. .................... 522/4 |
| 6,089,740 A | * | 7/2000 | Forehand et al. ........... 362/573 |
| 6,095,812 A | * | 8/2000 | Senn et al. .................... 433/29 |
| 6,103,203 A | * | 8/2000 | Fischer ...................... 422/186 |
| 6,282,013 B1 | * | 8/2001 | Ostler et al. ................. 359/309 |

FOREIGN PATENT DOCUMENTS

| | | |
|---|---|---|
| DE | 32 15 664 A1 | 10/1983 |
| DE | 38 40 984 A | 6/1990 |
| EP | 0 948 944 | 10/1999 |

OTHER PUBLICATIONS

K.-J. Reinhardt Der Einfluss der Lichtquelle auf die Randständigkeit von Kompositfüllungen Carl Hanser Verlag, München, 1991.

* cited by examiner

Primary Examiner—Ralph A. Lewis
(74) Attorney, Agent, or Firm—John C. Thompson; Alan S. Korman (57) ABSTRACT

A light curing device has a light source for curing light-polymerizable dental materials. A control circuit controls the light output of the light source according to a pre-determined output profile. The output profile has a starting time period with a decreased output relative to a maximum output, followed by a main curing time period. In the main curing time period, a pulsed output with alternating high output value and low output value is provided.

14 Claims, 6 Drawing Sheets

LIGHT CURING DEVICE AND METHOD FOR CURING LIGHT-POLYMERIZABLE DENTAL MATERIAL

This application claims the benefit of No. 60/146,590, Jul. 30, 1999.

BACKGROUND OF THE INVENTION

The present invention relates to a light curing device and method for curing light-polymerizable dental materials. The device comprises a light source with which the light-polymerizable dental materials are cured. Apparatus of this type is known from U.S. Pat. Nos. 6,095,812 and 6,123,545 the subject matter of said patent applications being incorporated herein by reference thereto. A control circuit is provided for controlling light distribution according to a pre-determined output profile. In accordance with this invention the output profile is controlled to have a start-up period, followed by a main curing period.

A number of light curing devices are known which attempt by various means to achieve a curing effect that is as good as possible and attempt to avoid the creation of open margins. It has been known from the printed publication "K.-J. Reinhardt: Der Einfluss der Lichtquelle auf die Randständigkeit von Kompositfüllungen", Carl Hanser Verlag, München, 1991, that light sources of a high light intensity have the propensity to create open margins.

In order to delay the Trommsdorff effect, it has further been suggested to provide a decreased light output value at the start of the entire lighting period in order to ensure that the viscosity of the dental material does not increase too fast.

A further problem of dental materials is their final curing grade (hardness). In order to achieve a satisfactory result, it has already been suggested to increase the light output step-wise over the length of the entire curing duration.

Despite these attempts, the shrinkage value has so far been unsatisfactory with known light curing devices.

Furthermore, light curing devices have been known for a long time with which the light output shall be provided by means of a Xenon flash lamp. With such light curing devices, the duration of voltage application of each light impulse lasts only 0.1 to 2 milliseconds, insofar reference is made, for example, to DE-OS 32 15 664.

Studies with such light curing devices have, however, led to the result that the curing effect is unsatisfactory so that such devices have not found acceptance in practice. Moreover, because of its size, the Xenon flash lamp which is of a usually complicated design is mostly suitable for stationary devices, with respect to which reference is also made to the aforementioned publication.

Therefore, it is an object of the present invention to provide a light curing device of the aforementioned kind with which the curing shrinkage and the temperature induced stress are reduced for curing light-polymerizable dental materials. By means of the low shrinkage value, the marginal integrity (marginal adaptation) shall be improved when curing composites.

SUMMARY OF THE INVENTION

This object is solved by the output profile showing a pulsed output with alternating high output value and low output value.

Accordingly, the inventive light-curing device, having a starting time period with an increase in the light output, is combined with a main curing time period during which the light output is alternated at an alternating high and low output value. Surprisingly, this combination results in a decreased curing shrinkage. Apparently, the time period of low light output allows the material to flow against the cavity edge. A gentle curing is achieved, and the propensity for the creation of open margins is reduced by the inventive light curing device. A factor that may also contribute to this result is that the temperature-induced stress is significantly reduced because of the pulsating action in comparison to conventional light curing devices.

While the earlier mentioned studies according to the publication of K. J. Reinhardt show the introduction of stresses due to high light intensity, studies based on the inventive device have surprisingly shown that the inventive short-term high light output is by no means detrimental, but that it favorably affects the hardness of the cured dental material.

A further favorable feature with respect to the invention is that the dental material becomes significantly less warm on curing in comparison to the continuous irradiation at a high light output. During a curing duration of 40 seconds, the temperature increase only amounts to 7° C. (when curing 25 $mm^3$ Tetric Ceram, a light-curing composite of the Vivadent company).

It is particularly advantageous according to the invention if the curing application is performed with a not too long alternating period between the high and the low output value. The alternating period can, for example, last for 2 seconds. With alternating periods in this range, the most favorable values result for the final hardness, on the one hand, and the curing shrinkage, on the other hand An advantageous embodiment of the invention provides to use an incandescent lamp as a light source. An incandescent lamp has a certain inertia with respect to the light radiation. The delay ranges between 100 milliseconds and up to almost one second with larger lamps. Moreover, the internal resistance of a cold spiral filament is significantly higher than the internal resistance of a hot spiral filament, so that usually an electrical connection impulse has to be handled on alternating electrical connection/disconnection pulses, i.e., on changes between an electrically fully connected and an electrically fully disconnected incandescent lamp. This alternation of a connection/disconnection pulse also puts stress on the spiral filament, resulting in a decreased service life.

In order to avoid this result, it is particularly advantageous if a slanted connecting flank is used for the transition between the low light output and the high light output. The fact that the commercially available halogen lights have a light output which is, for example, reduced by 60% at a 30% reduced electrical power can be especially favorably taken advantage of for the present invention. Due to the distinctly lower temperature of the spiral filament at a reduced luminous power, the emission of light is more than proportionally lowered. This often undesired behavior of spiral filaments can be particularly favorably taken advantage of, according to the invention, for the recovery periods of the light-polymerizable dental materials. A reduction of the electrical power by 30%, for example, accordingly results in a reduction of the light output by 60% or 70% which is sufficient for providing the recovery period.

According to a further, particularly favorable aspect of the invention, it is provided to select the starting time as to be comparatively rather long, for example, up to 0 40% of the entire lighting duration, so that the main curing time is 60% of the entire lighting duration. An especially favorable pre-curing effect and a uniform curing effect result therefrom. According to the invention, the core curing can be especially favorably affected by the combination of the relatively long starting time with the pulsating main curing time.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENT

Figure 4:
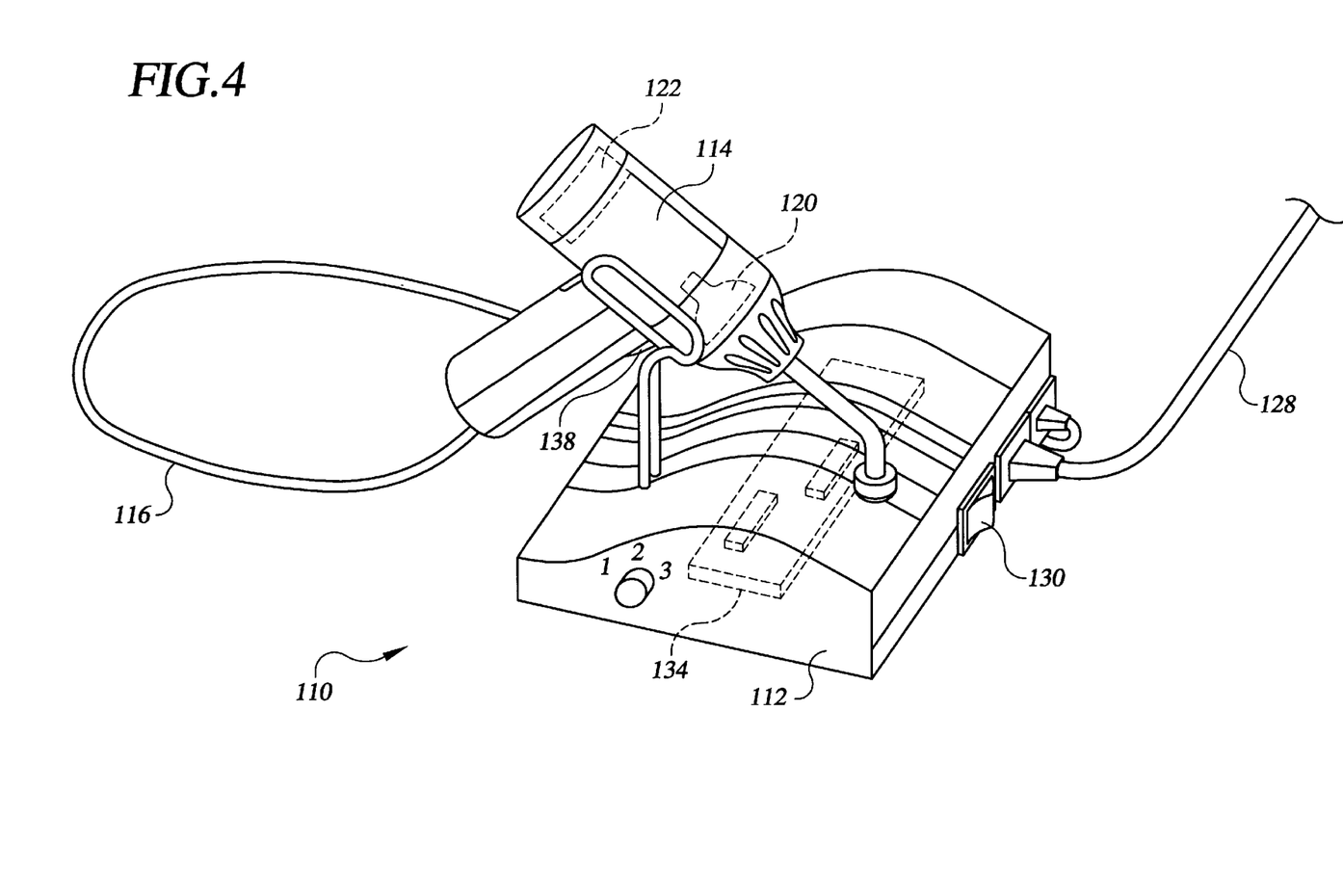
FIG. 4 is a perspective view of a light curing device in which the present invention may be incorporated.

Initially, with reference to FIG. 4, the present invention may be embodied in a light curing device indicated generally at 110, which light curing device includes a supply station 112 and a pistol shaped hand-held instrument 114 connected to one another by an electrical cable 116. The hand-held instrument includes housing 118, a light guide 119, a light source 120, and a fan 122. The supply source 112 is connected to electrical mains by power cord 128, and the power to the supply station may be turned "on" and "off" by an on/off switch 130.

Figure 5:
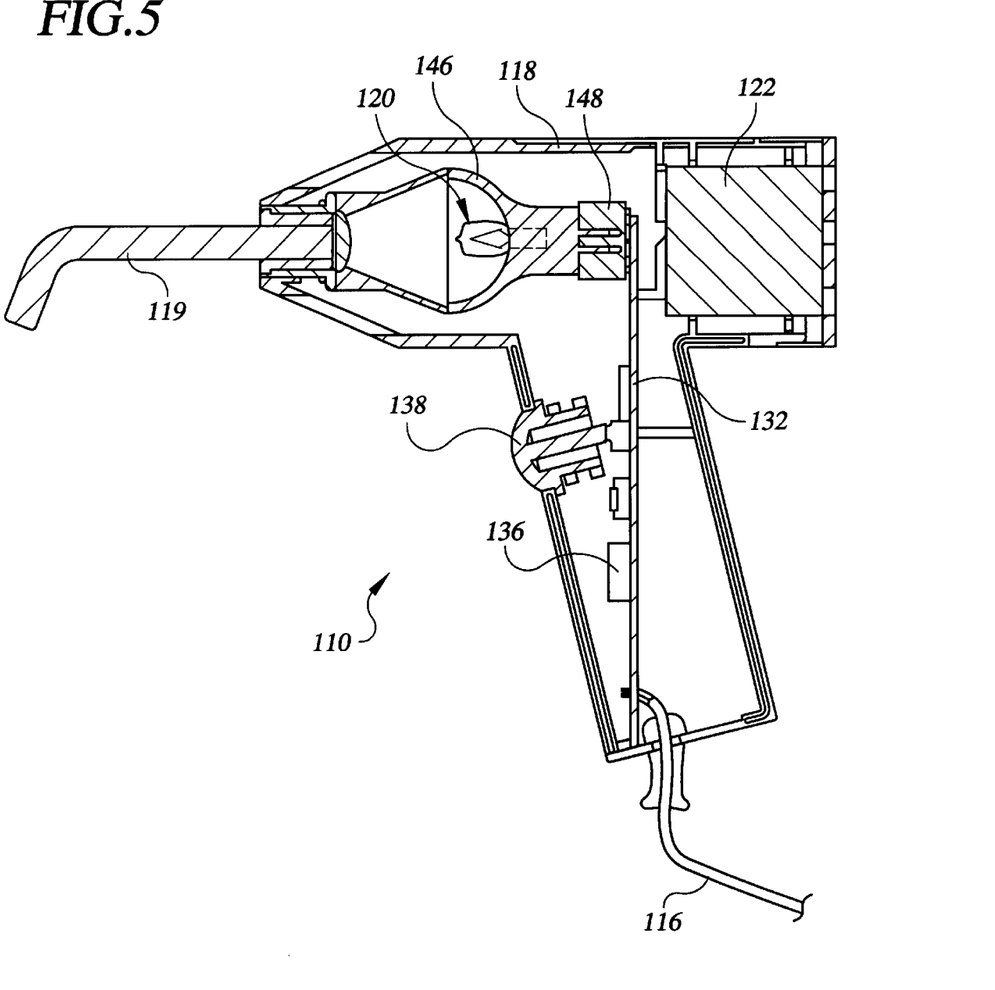
FIG. 5 is a sectional view of the hand held instrument shown in FIG. 4.

A control circuit is provided which includes in addition to cable 116 a printed circuit board 132 in the hand-held device 114 and another printed circuit board 134 in the supply station, one of which may be provided with a PID controller, indicated at 136 in FIG. 5.

The fan 122 may be on at all times when switch 130 is in its "on" position. Alternatively, it may be under the control of a further on/off switch 138 on the hand-held instrument, which switch may also initiate current flow to the lamp 120.

Figure 6:
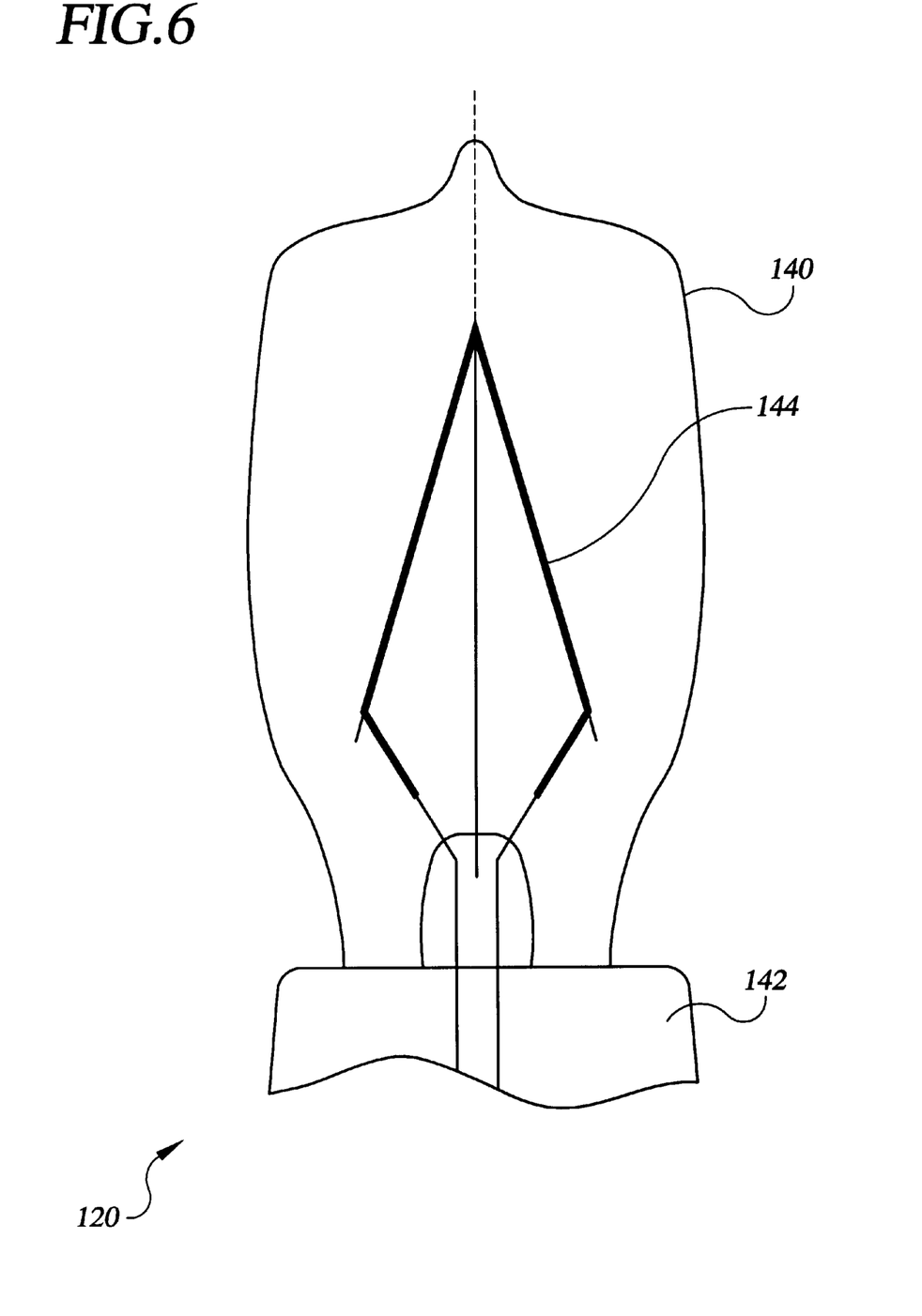
FIG. 6 is a side view of a halogen lamp which may be used in the hand held device shown in FIG. 5.

In the embodiment illustrated the light source may be a halogen lamp, shown in detail in FIG. 6, which halogen lamp includes a bulb 140 carried by a base 142, there being a spiral wound filament 144 in the bulb. The lamp 120 is mounted in a socket in a reflector assembly 146 which is in turn received by receiving socket 148 on the printed circuit board 132.

The present invention will now be described in detail with the aid of several specific embodiments utilizing FIGS. 1 through 3.

Figure 1:
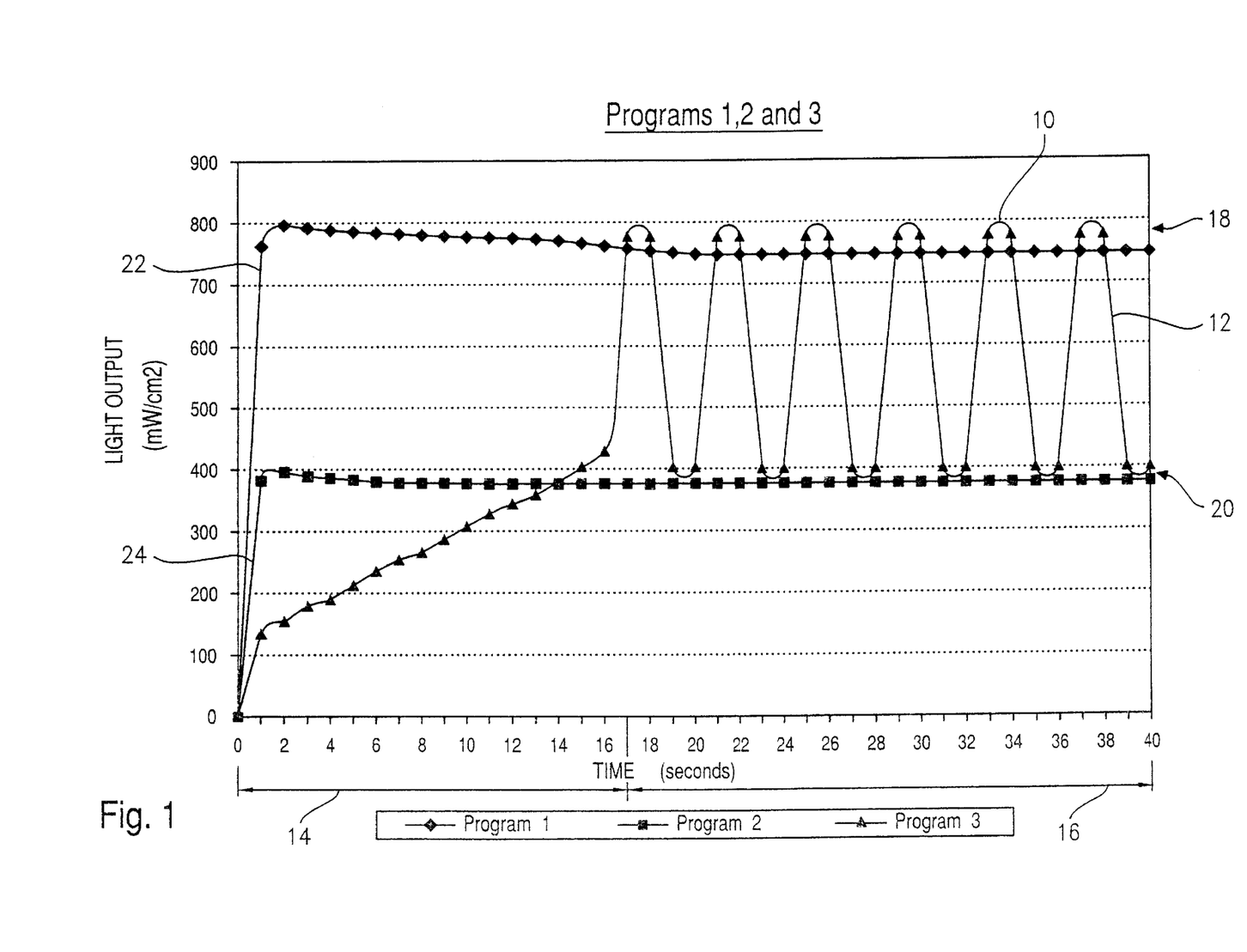
FIG. 1 shows a diagram of an output profile for illustrating the emitted light output, wherein the inventive output profile is compared with two known output profiles.

The output profile 10 illustrated in FIG. 1 shows the measured light output of a light curing device with three programs, whereby one embodiment of the inventive light curing device shows the output profile designated as program 3.

The output profile 10 is illustrated as a curve 12 of the light output. The applied electrical power which is not illustrated in FIG. 1 has to be distinguished therefrom. In the preferred embodiment, the applied electrical power results in the curve 12, whereby it is preferred that this curve is provided by a control of the electrical power.

According to the invention, it is particularly advantageous to increase the light output continuously during a starting time period 14 and to vary the light output between a high output value 18 and a low output value 20 during the main curing time 16. During the main curing time, the electrical power is, however, not substantially sinusoidal like the emitted light output, but shows at least steeper declining flanks, while the incandescent lamp 120 used as a light source cools down more slowly than would be proportional to the corresponding decline of the applied power.

It is understood that this dead time is inventively encompassed in the control of the control circuit 132–136.

Apart from the inventive control according to the curve 12, the inventive light curing device has two further output profiles according to the curves 22 and 24. The curve 22 shows a steep incline of the light output up to the high output value 18, the maximum value, and subsequently a flat decline and maintaining of that level essentially during the entire curing duration. In contrast thereto, the curve 24 shows a slightly less steep incline approximately up to the lower output value 20. It is possible with an inventive light curing device to select at one's choice curve 22 by program 1, curve 24 by program 2, and curve 12 by program 3. With programs 1 and 2 according to curves 22 and 24, the supply voltage for the light source is maintained at a constant level so that a relatively high connecting current is present due to the internal resistance of the light source, the connecting current being slightly flatter, corresponding to the inclining sides of the curves 22 and 24.

In contrast thereto, the incline angle of curve 12 with the inventive output profile 10 is significantly flatter. During a starting period which lasts 15 seconds of the entire lighting duration of 40 seconds, the emitted light output is first increased to 150 mW/cm$^2$ for approximately one second. Between the time of one second and 15 seconds, a controlled increase of the light output takes place from 150 mW/cm$^2$ to approximately 400 mW/cm$^2$, thus, approximately to the lower output value.

The main curing time 16 follows during the time period of 15 seconds to 40 seconds. The light output is initially increased between 15 seconds and 17 seconds from approximately 400 mW/cm$^2$ to the high output value, namely, approximately 800 mW/cm$^2$ and subsequently declines to the low value 20 until 19 seconds have elapsed. The light output essentially follows a waveshaped curve, and, during the main curing time 16, the curve 12 forms six wave-shaped curves or 12 alternations between the high and the low output values 18 and 20. It is understood that the exact output profile can be adjusted to the requirements in wide ranges and can, in particular, be adjusted by program-control depending on the curing objective.

Figure 2:
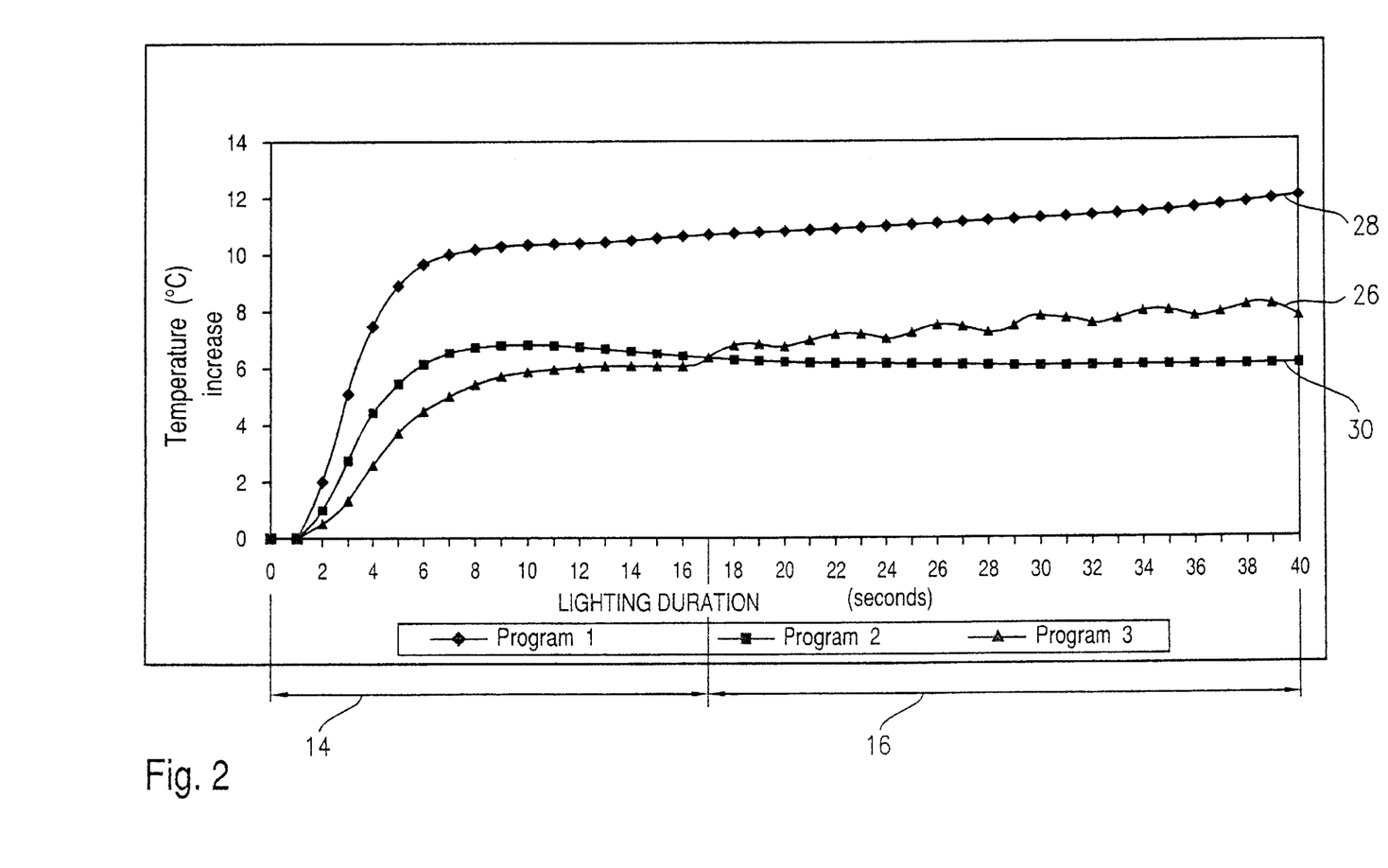
FIG. 2 another diagram for illustrating the temperature increase during the lighting duration.

FIG. 2 shows that the inventive control of the light curing device with the output profile according to curve 12 causes a distinctly lower temperature increase than with program 1. The curves of the programs 1, 2, and 3 are designated by reference numerals 26, 28, and 30. The inventive output profile 10 results in the temperature curve 26, thus, in a temperature increase by approximately 7° C. as a final value (when curing 25 mm$^3$ Tetric Ceram, a light curing composite of the Vivadent company), while program 1 causes a temperature increase by 12° C. It is apparent that the temperature curve 26 has a slightly wave-shaped inclining character during the main curing time 16, while curve 30 shows a maximum value of almost 7° C. at an elapsed time of 9 seconds of the entire lighting duration and subsequently declines, and the temperature curve 28 reaches a temperature increasing value of slightly more than 10° C. after approximately 8 seconds and subsequently slowly increases to 12° C.

Thus, according to the invention, the temperature increase stressing the dental material and affecting the patient is distinctly lower than with the temperature curve 28 and approximately in the area of temperature curve 30.

Furthermore, the core curing depth and the shrinkage measured as the Vickers pyramid hardness have been determined in studies of the inventive device. With all three programs, core curing depths resulted of approximately 5 mm, with program 1 having the deepest and program 2 the lowest core curing depth. However, the core curing depth was sufficient in all cases. Also the Vickers pyramid hardness did not show significant deviations between the individual programs. The measured curing values which showed a range between one and two percent, showed the following curing values according to the following chart:

| Program | Vickers pyramid hardness (HV 0.5130) (N/mm$^2$) |
|---------|-------------------------------------------------|
| 1       | 584                                             |
| 2       | 572                                             |
| 3       | 574                                             |

The Vickers pyramid hardness measurements show that comparable curing results are achieved with all three programs. The results do not differ statistically.

Because of the sample variation, no significant statement can be made with reference to curing differences.

Figure 3:
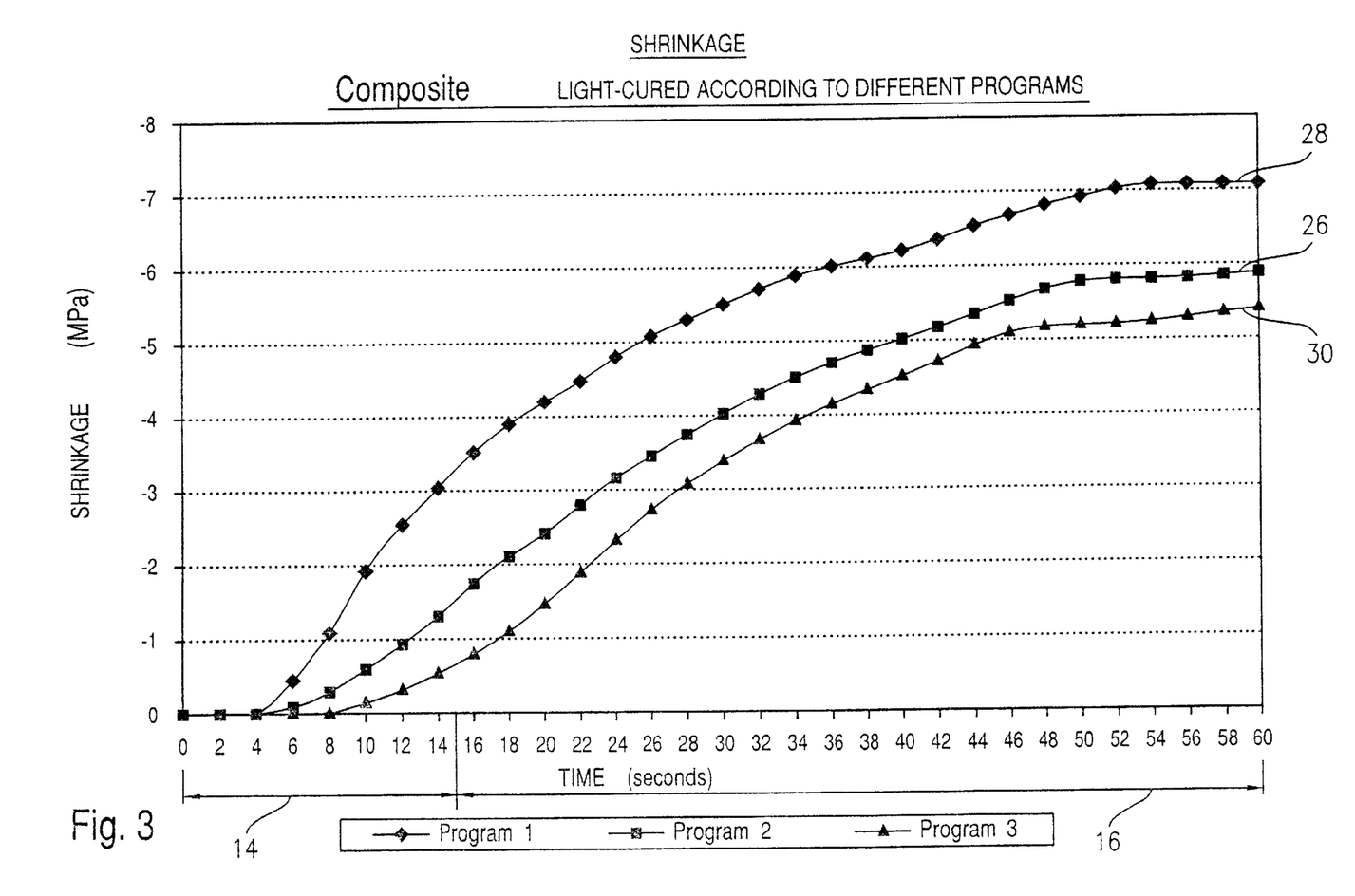
FIG. 3 a diagram for illustrating the shrinkage during the lighting duration.

FIG. 3 illustrates the shrinkage for the individual programs. The shrinkage curve clearly shows the positive effect of program 3. The slow-speed curing at the low light output value results in a slow-speed increase of the shrinkage which can have a positive effect on the marginal integrity of a filling.

A light source which employs a halogen lamp has been decribed above. However, it is possible that other light sources may be used in the practice of this invention. Thus it is possible to use either a laser diode, or an arrangement of LEDs.

What is claimed is:

1. A light curing device for directly curing light-polymerizable dental material with decreased curing shrinkage; said device comprising:

a light source for directly curing light-polymerizable dental materials, the light source capable of having light output values which vary between nil and a high light output value; and means to progressively control the output value of the light source during direct curing of the light-polymerizable dental material by initially increasing the light output value from nil to a low light output value of about 50% of the high light output value during a starting time period, and by subsequently varying the light output value between the low output value and the high light output value during a main curing time.

2. A light curing device according to claim 1, wherein said light source has a spiral filament and alternately emits light of greater and lesser intensity.

3. A light curing device according to claim 1, wherein said light output increases during said starting time period with an initial steep incline, followed by a flatter incline.

4. A light curing device according to claim 1, wherein the means to control the output of the light source is a control circuit, said control circuit constantly controlling said light output according to said output profile.

5. A light curing device according to claim 4, wherein said control circuit comprises a PID-controller, said PID controller taking into account a dead time of said light source.

6. A light curing device according to claim 4, further comprising a supply source and a hand-held instrument wherein said light source is mounted in said hand-held instrument, and wherein said control circuit is mounted in the supply source and has a control path extending between said hand-held instrument and said supply source.

7. A light curing device according to claim 6, wherein said control path is an electric cable.

8. A light curing device according to claim 1, wherein curve flanks of said output profile for an output increase from said low output value to said high output value have a slant corresponding to more than 10% of a pulsation period of said output profile during said main curing time period.

9. A light curing device according to claim 1, wherein said light source is a halogen lamp that continues to emit light during period durations of light emissions at said low/output value.

10. A light curing device according to claim 1, wherein said light source is a laser diode.

11. A light curing device according to claim 1, wherein said light source is an arrangement of LEDs.

12. A light curing device for directly curing a light-polymerizable dental material with decreased curing shrinkage comprising:

a light source for directly curing light-polymerizable dental materials, the light source capable of having light output values which vary between nil and a high light output value; and means to progressively control the output value of said light source according to a pre-determined output profile, wherein said output profile has a starting time period of not less than 10 seconds with an initial output value of nil and a final low output value of about 50% of the high light output value, followed by a main curing time period of at least 20 seconds; and wherein in said main curing time period a pulsed output value with alternating high light output value and low light output value is provided.

13. A light curing device according to claim 12, wherein a sequence of said high light output value and said low output value is periodic during said main curing time with periodic durations ranging between 3 and 5 seconds.

14. A process for curing by light a light-polymerizable dental material with decreased curing shrinkage; the process including:

providing a light source for curing the light-polymerizable dental material, the light source capable of having light output values which vary between nil and a high light output value;

controlling the output value of the light source progressively to initially increase the light output value from nil to a low light output value of between 25% and 60% of said high light output value during a starting time period, and to subsequently vary the light output value between the low output value and the high light output value during a main curing time.

\* \* \* \* \*

UNITED STATES PATENT AND TRADEMARK OFFICE
CERTIFICATE OF CORRECTION

PATENT NO.    : 6,482,004 B1
DATED         : November 19, 2002
INVENTOR(S)   : Bruno Senn et al.

It is certified that error appears in the above-identified patent and that said Letters Patent is hereby corrected as shown below:

Column 6,
Line 9, "," should be inserted after "instrument"
Line 23, "low/output" should be changed to -- low output --.
Line 66, add the following claims:
15.    A process for curing by light a light-polymerizable dental material according to claim 14, wherein said low output value is adjusted such that an emitted light output value is about 50% of said high light output value during a starting time period.
16.    A process for curing by light a light-polymerizable dental material according to claim 14, wherein a sequence of said high light output value and said low output value is periodic during said main curing time with periodic durations ranging between 0.01 and 15 seconds.
17.    A process for curing by light a light-polymerizable dental material according to claim 14, wherein a sequence of said high light output value and said low output value is periodic during said main curing time with periodic durations ranging between 3 and 5 seconds.
18.    A process for curing by light a light-polymerizable dental material according to claim 14, wherein curve flanks of said output value profile for an output value increase from said low output value to said high light output value have a slant corresponding to more than 10% of a pulsation period of said output value profile during said main curing time period.

Signed and Sealed this

Sixteenth Day of September, 2003

JAMES E. ROGAN
*Director of the United States Patent and Trademark Office*